United States Patent
St. Laurent et al.

(10) Patent No.: US 9,440,916 B2
(45) Date of Patent: Sep. 13, 2016

(54) 3, 4-BIS-BENZYLSULFONYLBUTYRONITRILE AND ITS PHARMACEUTICAL USE

(71) Applicant: Olatec Therapeutics LLC, New York, NY (US)

(72) Inventors: Joseph P. St. Laurent, Lakeville, MA (US); Gerald S. Jones, Norwood, MA (US); David M. Bresse, Middleboro, MA (US); Scott A. Goodrich, Stoughton, MA (US)

(73) Assignee: OLATEC THERAPEUTICS LLC, New York, NY (US)

( * ) Notice: Subject to any disclaimer, the term of this patent is extended or adjusted under 35 U.S.C. 154(b) by 0 days.

(21) Appl. No.: 15/078,179

(22) Filed: Mar. 23, 2016

(65) Prior Publication Data

US 2016/0200675 A1    Jul. 14, 2016

Related U.S. Application Data

(63) Continuation-in-part of application No. PCT/US2014/057521, filed on Sep. 25, 2014.

(60) Provisional application No. 61/883,129, filed on Sep. 26, 2013, provisional application No. 62/138,815, filed on Mar. 26, 2015.

(51) Int. Cl.
| | |
|---|---|
| *C07C 317/28* | (2006.01) |
| *C07C 315/02* | (2006.01) |
| *C07C 319/12* | (2006.01) |
| *A61K 9/06* | (2006.01) |

(52) U.S. Cl.
CPC .......... *C07C 317/28* (2013.01); *C07C 315/02* (2013.01); *C07C 319/12* (2013.01)

(58) Field of Classification Search
None
See application file for complete search history.

(56) References Cited

U.S. PATENT DOCUMENTS

| | | | |
|---|---|---|---|
| 3,166,582 A * | 1/1965 | Carboni | C07D 207/456 546/153 |
| 3,792,093 A | 2/1974 | Bullock | |
| 5,180,852 A | 1/1993 | Shaw | |
| 6,063,778 A | 5/2000 | Kim et al. | |
| 2012/0157524 A1 | 6/2012 | St. Laurent | |

OTHER PUBLICATIONS

International Search Report dated Dec. 16, 2014 in PCT/US2014/57521.

* cited by examiner

*Primary Examiner* — Yevegeny Valenrod
(74) *Attorney, Agent, or Firm* — Perkins Coie LLP; Viola T. Kung

(57) ABSTRACT

The present invention is directed to a method of treating an inflammatory skin disease or disorder, such as dermatitis, psoriasis, acne, or rosacea. The method comprises administering to the subject 3, 4-bis-benzylsulfonylbutyronitrile in an amount effective to reduce or eliminate the symptoms of the inflammatory skin disease or disorder. Topical administration and oral administration are preferred route of administration.

9 Claims, 1 Drawing Sheet

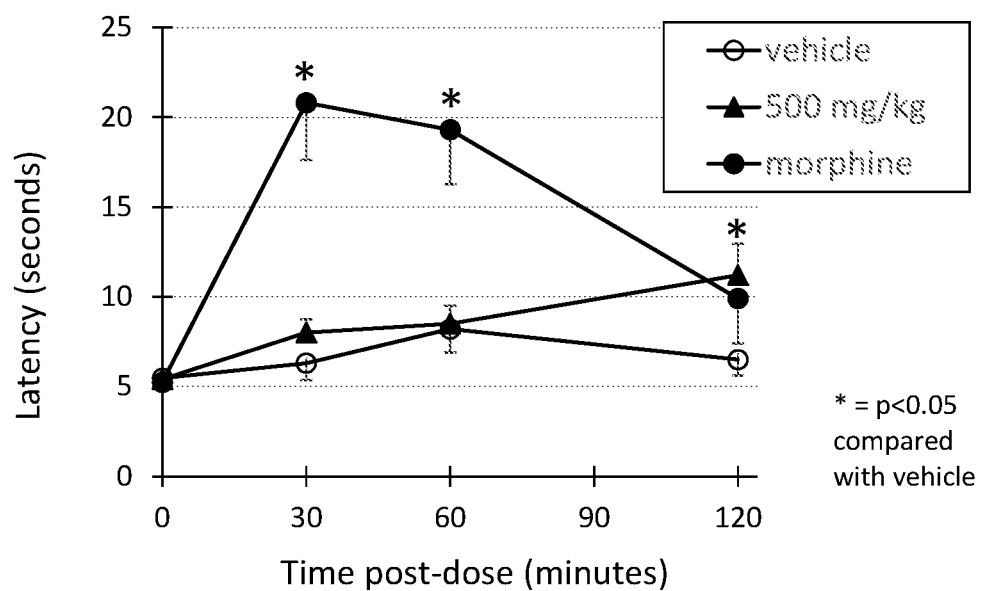

3, 4-BIS-BENZYLSULFONYLBUTYRONITRILE AND ITS PHARMACEUTICAL USE

This application is a continuation-in-part of PCT/US2014/057521, filed Sep. 25, 2014, which claims the priority of U.S. Provisional application No. 61/883,129, filed Sep. 26, 2013. This application also claims the benefit of U.S. Provisional application No. 62/138,815, filed Mar. 26, 2015. The above-identified applications are incorporated herein by reference in their entireties.

FIELD OF THE INVENTION

The present invention relates to 3, 4-bis-benzylsulfonyl-butyronitrile and a pharmaceutical composition comprising same. The present invention also relates to methods of using the compound for treating inflammation or inflammatory-related disorders and pain. The present invention further relates to methods of using 3, 4-bis-benzylsulfonylbutyronitrile, or its pharmaceutically acceptable salts, for treating skin inflammatory diseases.

BACKGROUND OF THE INVENTION

Inflammation is a process by which microbes or tissue injury induce the release of cytokines and chemokines from various cell types producing increased blood vessel permeability, upregulation of endothelial receptors, and thus increased egress of various cells of the innate and adaptive immune system which enter surrounding tissue and grossly produce the classical picture of inflammation, i.e. redness, swelling, heat and pain.

Inflammation is a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is often followed by an altered structure and penetrability of the cellular membrane. Endogenous factors, such as mediators and antigens define the nature and type of an inflammatory reaction, especially its course in the zone of injury. In the case where tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also provide the course of inflammatory process on a molecular level by damaging cellular membranes which initiate biochemical reactions.

Based on the physical causes, pain can be divided into three types: nociceptive, neuropathic, and mix-type.

Nociceptive pain is the term for pain that is detected by nociceptors. Nociceptors are free nerve endings that terminate just below the skin, in tendons, in joints, and in internal organs. Nociceptive pain typically responds well to treatment with opioids and NSAIDs. There are several types of nociceptive pain: somatic pain, visceral pain, and cutaneous pain. Visceral pain comes from the internal organs. Deep somatic pain is initiated by stimulation of nociceptors in ligaments, tendons, bones, blood vessels, fasciae and muscles, and is dull, aching, poorly localized pain. Examples include sprains and broken bones. Superficial pain is initiated by activation of nociceptors in the skin or other superficial tissue, and is sharp, well-defined and clearly located. Examples of injuries that produce superficial somatic pain include minor wounds and minor (first degree) burns. Nociceptive pain is usually short in duration and ends when the damage recovers. Examples of nociceptive pain include postoperative pain, sprains, bone fractures, burns, bumps, bruises, and inflammatory nociceptive pain. Inflammatory nociceptive pain is associated with tissue damage and the resulting inflammatory process.

Neuropathic pain is produced by damage to the neurons in the peripheral and central nervous systems and involves sensitization of these systems. Because the underlying etiologies are usually irreversible, most of neuropathic pain are chronic pain. Most people describe neuropathic pain as shooting, burning, tingling, lancinating, electric shock qualities, numbness, and persistent allodynia. The nomenclature of neuropathic pain is based on the site of initiating nervous system with the etiology; for examples, central post-stroke pain, diabetes peripheral neuropathy, post-herpetic (or post-shingles) neuralgia, terminal cancer pain, phantom limb pain.

Mix-type pain is featured by the coexistence of both nociceptive and neuropathic pain. For example, muscle pain trigger central or peripheral neuron sensitization leading to chronic low back pain, migraine, and myofacial pain.

Connective tissues are subjected to a constant barrage of stress and injury. Acute or chronic impacts and the natural progression of various degenerative diseases all produce painful inflammation in joint regions, such as the neck, back, arms, hips, ankles and feet. These afflictions are common and often debilitating.

There is a need for a composition and a method for treating inflammation, inflammatory-related disorders, and pain. The composition should be economic and easy to manufacture, and the method should be effective and have no significant side effects.

BRIEF DESCRIPTION OF THE DRAWINGS

FIG. 1 shows the results of tail flick test of mice treated with vehicle (DMSO, oral application), test compound (500 mg/kg in DMSO, oral application) and morphine (in water, subcutaneous application). The latency time of each group is calculated as mean±SEM and plotted against time, where * indicates p value <0.05 compared with vehicle-treated mice.

DETAILED DESCRIPTION OF THE INVENTION

Definitions

An "enantiomer" is one of two stereoisomers that are mirror images of each other that are non-superposable (not identical). Organic compounds that contain a chiral carbon usually have two non-superposable structures.

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

A "Racemate" is a mixture that has equal amounts of left- and right-handed enantiomers of a chiral molecule.

"Solvates," as used herein, are addition complexes in which the compound is combined with an acceptable co-solvent in some fixed proportion. For the compound of the present invention, co-solvents include, but are not limited to, water, ethanol, and acetic acid.

3, 4-Bis-benzylsulfonylbutyronitrile

The inventors have isolated and identified 3, 4-bis-benzylsulfonylbutytonitrile or a pharmaceutically acceptable salt, solvate, an enantiomer, or enantiomers thereof. The compound or its pharmaceutically acceptable, solvate, an enantiomer, or enantiomer is effective for treating inflammation, inflammatory-related disorders, and pain. 3, 4-Bis-benzylsulfonylbutyronitrile, also called 3, 4-bis-benzylsulfonylbutanenitrile, has molecular weight of 377.48 and its structure is shown below, where "*" denotes a chiral carbon that allows for the existence of optically active enantiomers.

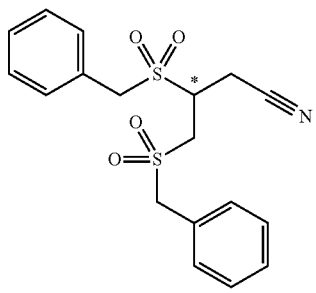

3, 4-bis-benzylsulfonylbutanenitrile 3,4-Bis-benzylsulfonylbutyronitrile can be synthesized by peroxide oxidation of the corresponding bis-sulfide, which can be isolated after treatment of 4-bromo-2-butenenitrile with benzyl mercaptan under basic conditions. The requisite 4-bromo-2-butenenitrile can be prepared by bromination of allyl cyanide to give 3,4-dibrobutane nitrile, followed by base-catalyzed elimination of HBr to introduce a double bond between C2 and C3, which is expected to be an approximately 1:1 mixture of E- and Z-isomers. Subsequent addition of benzyl mercaptan, then, is expected to result in an approximately 1:1 mixture of enantiomers of the bis-sulfide which, upon oxidation with peroxide, affords 3,4-bis-benzylsulfonylbutyronitrile as an enantiomeric mixture.

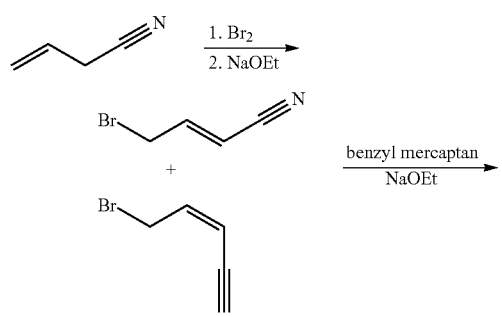

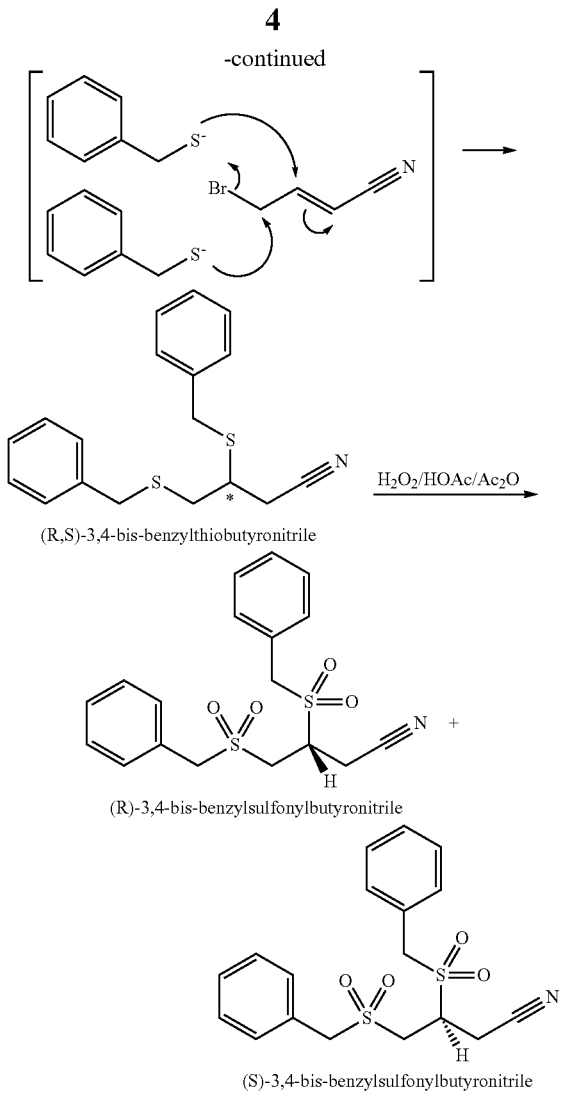

The present invention is directed to a method for preparing 3,4-bis-benzylsulfonylbutyronitrile. The method comprising the steps of: (a) reacting benzyl mercaptan with 4-bromo-2-butenenitrile in a basic condition to produce 3,4-bis-benzylthiobutyronitrile, and (b) oxidizing 3,4-bis-benzylthiobutyronitrile with peroxide to produce 3,4-bis-benzylsulfonylbutyronitrile. In step (a), a basic condition is required to generate benzyl mercaptide, which is an intermediate. Any base that is compatible with the solvents in the reaction can be used; a preferred base is an ethanolic solution of sodium ethoxide, which can be prepared by dissolving sodium metal in ethanol.

The method further comprises a step (i), before the above step (a), of preparing the requisite 4-bromo-2-butenenitrile by reacting bromine ($Br_2$) with allyl cyanide in a basic condition. In step (i), allyl cyanide is brominated in organic solvents such as petroleum ether and alcohol, and then HBr is eliminated from the molecule to form a double bond in a basic condition. In one embodiment, step (i) and step (a) is a one-pot reaction.

In the above steps (a) and (i), any base that is compatible with the solvents in the reaction mixture can be used; a preferred base is an ethanolic solution of sodium ethoxide, which can be prepared by dissolving sodium metal in ethanol.

Pharmaceutical Compositions

The present invention provides pharmaceutical compositions comprising one or more pharmaceutically acceptable carriers and a compound of 3, 4-bis-benzylsulfonylbutanenitrile, or a pharmaceutically acceptable salt, or an enantiomer, or enantiomers thereof. The pharmaceutical composition can include one of the enantiomers, or both enantiomers either equimolar as a racemate, or of different amounts. For abbreviation, "an active compound," when used in this application, is meant to include 3, 4-bis-benzylsulfonylbutanenitrile, or a pharmaceutically acceptable salt, or an enantiomer, or enantiomers thereof. The active compound in the pharmaceutical compositions in general is in an amount of about 0.01-20%, or 0.05-20%, or 0.1-20%, or 0.2-15%, or 0.5-10%, or 1-5% (w/w) for a topical formulation; about 0.1-5% for an injectable formulation, 0.1-5% for a patch formulation, about 1-90% for a tablet formulation, and 1-100% for a capsule formulation.

In one embodiment, the active compound is incorporated into any acceptable carrier, including creams, gels, lotions or other types of suspensions that can stabilize the active compound and deliver it to the affected area by topical applications. In another embodiment, the pharmaceutical composition can be in a dosage form such as tablets, capsules, granules, fine granules, powders, syrups, suppositories, injectable solutions, patches, or the like. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet or a capsule may include fillers, binders, lubricants and glidants, disintegrators, wetting agents, and release rate modifiers. Binders promote the adhesion of particles of the formulation and are important for a tablet formulation. Examples of excipients of a tablet or a capsule include, but not limited to, carboxymethylcellulose, cellulose, ethylcellulose, hydroxypropylmethylcellulose, methylcellulose, karaya gum, starch, tragacanth gum, gelatin, magnesium stearate, titanium dioxide, poly(acrylic acid), and polyvinylpyrrolidone. For example, a tablet formulation may contain inactive ingredients such as colloidal silicon dioxide, crospovidone, hypromellose, magnesium stearate, microcrystalline cellulose, polyethylene glycol, sodium starch glycolate, and/or titanium dioxide. A capsule formulation may contain inactive ingredients such as gelatin, magnesium stearate, and/or titanium dioxide.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

In one embodiment, lauryl lactate (for example, at about 0.1-10%, or about 0.2-5%, or about 0.5-5%) is included in the topical gel formulation. Lauryl lactate is considered safe for topical administration. Lauryl lactate is qualified for human use within pharmaceutical and cosmetic products. Lauryl lactate when used in a topical formulation enhances the permeability of the compound. Preferably lauryl lactate is purified to achieve ≥90%, preferably ≥95% purity; the high purity mitigates the presence of hydrolytic and oxidative agents. In addition, DMSO at 0.1-20%, or 0.5-10% (w/w) in the formulation provides suitable solubility of the active compound.

In another embodiment, diethylene glycol monoethyl ether is included in the topical gel formulation.

Method of Use

Inflammation is a process and a state of tissue pathology resulting from activation and continuation of activity of the innate and acquired components of the immune system. The arachidonic acid cascade and cytokine production and action in cell to cell interactions are critical components of immune activation and response, which lead to inflammation. Arachidonic acid is a component of membrane phospholipids.

After it is freed from phospholipids, arachidonic acid acts as a precursor to many of the known eicosinoids including prostaglandins and leucotrienes, which are known pro-inflammatory entities.

The active compound is anti-inflammatory when applied topically in the mouse ear swelling model, in which the inflammation is induced by arachidonic acid. The active compound is effective in inhibiting pro-inflammatory mediators.

The present invention is directed to a method of treating inflammation and/or pain. 3, 4-bis-benzylsulfonylbutanenitrile, can be used as is, or it can be administered in the form of a pharmaceutical composition that additionally contains a pharmaceutically acceptable carrier. The method comprises the steps of first identifying a subject suffering from inflammation and/or pain, and administering to the subject the active compound, in an amount effective to treat inflammation and/or pain. "An effective amount," as used herein, is the amount effective to treat a disease by ameliorating the pathological condition or reducing the symptoms of the disease.

In one embodiment, the method reduces or alleviates the symptoms associated with inflammation. The present invention provides a method to treat localized manifestations of inflammation characterized by acute or chronic swelling, pain, redness, increased temperature, or loss of function in some cases.

In another embodiment, the present invention provides a method to alleviate the symptoms of pain regardless of the cause of the pain. The general term "pain" treatable by the present method includes nociceptive, neuropathic, and mix-type. The present invention reduces pain of varying severity, i.e. mild, moderate and severe pain; acute and chronic pain. The present invention is effective in treating joint pain, muscle pain, tendon pain, burn pain, and pain caused by inflammation such as rheumatoid arthritis.

In one embodiment, the present invention is useful in treating inflammation and/or pain associated in a musculoskeletal system or on the skin. The highly innervated, musculoskeletal and skin systems have a high capacity for demonstration of pain. In addition, the musculoskeletal system has a high capacity for tissue swelling, and the skin has a high capacity for redness, swelling, and heat. In musculoskeletal and skin systems, the degree of tissue damage is frequently magnified out of proportion to the resulting inflammatory response. In the skin for example, merely firm stroking will cause release of the cytokines, IL-1 and TNF.

The present invention provides a method for treating inflammation and/or pain associated with inflammatory skeletal or muscular diseases or conditions. The method comprises the steps of identifying a subject in need thereof, and administering to the subject the active compound, in an amount effective to treat inflammation and/or pain. "The active compound," as used herein, is intended to include 3, 4-bis-benzylsulfonylbutanenitrile and its pharmaceutically acceptable salts, enantiomer, or enantiomers thereof. The skeletal or muscular diseases or conditions include musculoskeletal sprains, musculoskeletal strains, tendonopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

The present invention provides a method for treating inflammation and/or pain associated with inflammatory skin diseases such as dermatitis, psoriasis, and acne. The method comprises the steps of identifying a subject in need thereof, and administering to the subject the active compound, in an amount effective to treat inflammation and/or pain.

Skin is highly reactive to environmental stimuli and the epidermal component of keratinocytes is a very rich source of both arachidonic acid and pro-inflammatory cytokines of IL-1 and TNF. The skin dendritic cells, Langerhans cells, recognize and process antigens for further immune response of various lymphocytes and all of these cells are primarily regulated by cytokines through their specific cell surface receptors.

3, 4-Bis-benzylsulfonylbutanenitrile, which is effective in inhibiting arachidonic acid induced inflammation and inhibiting pro-inflammatory mediators, is effective to treat inflammation and/or pain associated with psoriasis, acne, rosacea, and dermatitis, particularly contact dermatitis, and atopic dermatitis. The present invention provides a method for treating inflammation and/or pain associated with inflammatory skin diseases such as psoriasis, acne, rosacea, and dermatitis, particularly contact dermatitis, and atopic dermatitis. The method comprises the steps of identifying a subject in need thereof, and administering to the subject the active compound, in an amount effective to treat inflammation and/or pain.

3, 4-Bis-benzylsulfonylbutanenitrile, which are effective in inhibiting arachidonic acid induced inflammation and in inhibiting the release of pro-inflammatory cytokine, are effective to treat inflammatory skin diseases such as dermatitis (atopic dermatitis), psoriasis, acne, and rosacea. The present invention provides a method for treating inflammatory skin diseases such as dermatitis, psoriasis, and acne (acne vulgaris). The method comprises the steps of identifying a subject in need thereof, and administering to the subject 3, 4-bis-benzylsulfonylbutanenitrile, or a pharmaceutically acceptable salt thereof, in an amount effective to reduce or eliminate the symptoms of the disease.

Dermatitis (also called eczema) is generic inflammation of the skin. Specific types of dermatitis include atopic, contact, nummular, and photo-induced.

Contact dermatitis is a localized rash or irritation of the skin caused by contact with a foreign substance. Only the superficial regions of the skin are affected in contact dermatitis. Inflammation of the affected tissue is present in the epidermis (the outermost layer of skin) and the outer dermis (the layer beneath the epidermis). Contact dermatitis results in large, burning, and itchy rashes. Contact dermatitis is an inflammatory condition of the skin either of irritant exposure to the skin without specific adaptive immunologic pathogenesis or of allergic sensitization and subsequent exposure of the skin to the sensitizing allergen with specific adaptive immunologic pathogenesis. Both involve innate and acquired immune system response including arachidonic acid and cytokine components that initiate and propagate the disease through cell to cell messaging by eicosanoid and/or cytokine moieties produced by epidermal cells, macrophages, dendritic cells, neutrophils, eosinophils, and various T and B lymphocytes. Contact dermatitis may be either acute or chronic. The acute forms are pruritic with erythema, edema, and micro or macrovesiculation in the areas of skin contact by the initiating factor. The chronic forms are pruritic with milder erythema, scaling, lichenification, and possibly fissuring particularly on the hands.

Allergic contact dermatitis is a T cell-mediated delayed type hypersensitivity reaction that occurs upon hapten challenge in sensitized individuals. The inflammatory response in classical allergic contact dermatitis requires both a sensitization phase and an elicitation phase responsible for the recruitment and activation of specific T cells at the site of hapten skin challenge.

Atopic dermatitis is a genetically determined disease that is part of the broader disease complex of atopy that includes asthma, hay fever, and atopic dermatitis. Many individuals with atopic dermatitis have various mutations of the filaggrin gene that codes for an important epidermal structural protein that when defective, results in abnormal barrier function of the epidermis. The altered barrier allows exposure to multiple environmental allergens that are first recognized by innate immune responses involving arachidonic acid and eicosanoids and recruitment of eosinophils, mast cells, and other inflammatory cells that initiate an acute responses of itch, erythema, and subsequent scratching and additionally activate the adaptive immune responses that involve inflammation by lymphocytes predominantly of a TH 2 derivation and activity. Atopic dermatitis is responsive to a number of cytokine inhibitors such as cyclosporine, and tacrolimus.

Current theory of the pathogenesis of psoriasis is that in individuals who are genetically susceptible a triggering event in the epidermis such as injury or super antigen contact initiates an response of the innate immune system with arachidonic acid and eicosanoid generation, recruitment and activity of neutrophils. Subsequent transformation of the response to that of a TH 1 adaptive immunity with cytokine activation and activity of specific T lymphocytes effect the pathological changes in the epidermis and dermis, which result in the typical psoriasis lesions of plaques that are erythematous, thickened, and scaly. Psoriasis is responsive to various immunomodulators including cyclosporine, methotrexate, and a host of specific biologicals that interfere with cytokine signaling.

Acne vulgaris, a progressively inflammatory disorder of the pilosebaceous follicular unit especially of the face and upper chest and back is a very common disease of both males and females after initiation of puberty, and in females even prior to adrenal gland maturity. Increased production of androgenic hormones by adrenal, ovarian, and testicular glands and by the pilosebaceous unit itself produce an increase in sebum and changes in its lipid composition, which combine with follicular epithelial cells to produce some degree of obstruction of the infra-infundibular portion of the pilosebaceous follicle resulting in the initial lesion of acne, the microcomedo. This consequent dilation of the pore and the changed composition of sebum at puberty facilitate colonization of the follicle by *Propionibacterium acnes* bacilli that produce enzymes to degrade the triglycerides in sebum to free fatty acids that leak through the follicle into the dermis and incite arachidonic acid pathways of eicosanoid production and subsequent initiation of inflammation. The bacilli also initiate chemokine production that attracts further inflammatory cells to the area and consequent cytokine production and action to continue and amplify inflammation. Thus initiation and propagation of progressive inflammation in the microcomedo produces the evolution to the several hallmark lesions of inflammatory acne, papule, pustule, nodule, and cyst. The present invention is useful to treat common acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne or acne medicamentosa.

Rosacea is a chronic condition characterized by facial erythema and sometimes pimples. Rosacea typically begins as redness on the central face across the cheeks, nose, or forehead, but can also less commonly affect the neck, chest, ears, and scalp. In some cases, additional symptoms, such as semi-permanent redness, telangiectasia (dilation of superficial blood vessels on the face), red domed papules (small bumps) and pustules, red gritty eyes, burning and stinging sensations, and in some advanced cases, a red lobulated nose (rhinophyma), may develop. There are 3 subtypes of rosacea that affect the skin: erythematotelangiectatic rosacea, papulopustular rosacea, and phymatous rosacea.

3, 4-Bis-benzylsulfonylbutanenitrile are effective in treating contact dermatitis and alleviating one or more symptoms selected from the group consisting of consisting of erythema, edema, lichenification, scaling, fissuring, and micro or macrovesiculation.

3, 4-Bis-benzylsulfonylbutanenitrile are effective in treating atopic dermatitis and alleviating one or more symptoms selected from the group consisting of erythema, induration, lichenification, scaling, and oozing and crusting.

3, 4-Bis-benzylsulfonylbutanenitrile are effective in treating psoriasis and alleviating erythema, scaling, and/or thickness of the psoriasis lesions.

3, 4-Bis-benzylsulfonylbutanenitrile are effective in treating acne and alleviating acne lesions selected from the groups consisting of closed comedones, papules, pustules, nodules, and cysts.

3, 4-Bis-benzylsulfonylbutanenitrile are effective in treating rosacea and alleviating one or more symptoms selected from the group consisting of erythema, telangiectasia, red domed papules and pustules, red gritty eyes, and burning and stinging sensations.

The pharmaceutical composition of the present invention can be applied by local administration and systemic administration. Local administration includes topical administration. Systemic administration includes oral, parenteral (such as intravenous, intramuscular, subcutaneous or rectal), and other systemic routes of administration. In systemic administration, the active compound first reaches plasma and then distributes into target tissues. Topical administration and oral administration are preferred routes of administration for the present invention.

Dosing of the composition can vary based on the extent of the injury and each patient's individual response. For systemic administration, plasma concentrations of the active compound delivered can vary; but are generally $1 \times 10^{10}$-$1 \times 10^{-4}$ moles/liter, and preferably $1 \times 10^{-8}$-$1 \times 10^{-5}$ moles/liter.

In one embodiment, the composition is applied topically onto the affected area and rubbed into it. The composition is topically applied at least 1 or 2 times a day, or 3 to 4 times per day, depending on the medical issue and the disease pathology being chronic or acute. In general, the topical composition comprises about 0.01-20%, or 0.05-20%, or 0.1-20%, or 0.2-15%, 0.5-10, or 1-5% (w/w) of the active compound. For example, the topical composition comprises about 1 or 5% (w/w) of the active compound. Depending on the size of the affected area, 0.2-85 mL, typically 0.2-10 mL, of the topical composition is applied to the individual per dose. The active compound passes through skin and is delivered to the site of discomfort.

In one embodiment, the pharmaceutical composition is administrated orally to the subject. The dosage for oral administration is generally at least 0.1 mg/kg/day and less than 100 mg/kg/day. For example, the dosage for oral administration is 0.1-100, or 0.5-50, or 1-20, or 1-10, or 1-50 mg/kg/day for a human subject. For example, the dosage for oral administration is 20-1000 mg/day, and preferably 20-500, 20-100, 25-200, 50-500, 50-200, 100-600, 100-400, or 200-800 mg/day for a human subject.

In one embodiment, the pharmaceutical composition is administrated intravenously to the subject. The dosage for intravenous bolus injection or intravenous infusion is generally 0.03 to 20 and preferably 0.03 to 10 mg/kg/day.

In one embodiment, the pharmaceutical composition is administrated subcutaneously to the subject. The dosage for subcutaneous administration is generally 0.3-20, and preferably 0.3-3 mg/kg/day.

Those of skill in the art will recognize that a wide variety of delivery mechanisms are also suitable for the present invention.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Example 1

Preparation of 3, 4-bis-benzylsulfonylbutanenitrile (A) A solution of allyl cyanide (0.59 mole) in t-amyl alcohol (120 mL) and pet ether (370 mL) was treated sequentially with a solution of bromine (0.59 mole) in t-amyl alcohol (60 mL), followed by an ethanolic solution of sodium ethoxide (345 mL, 0.60 mole). When the reaction mixture had cooled to room temperature, solids were removed by vacuum filtration and the filtrate was concentrated under reduced pressure. The residual liquid was charged on a silica gel column (307.10 g) and eluted with hexanes-ethyl acetate (19:1; 9:1). Combination of appropriate fractions, followed by concentration under reduced pressure gave 4-bromo-2-butenenitrile as a pale yellow liquid (47.14 g).

(B) The product from part (A) (8.9 mmol) was added dropwise to a solution of benzyl mercaptan (8.5 mmol) in ethanol (10 mL) containing sodium ethoxide (8.75 mmol). After stirring overnight, solids were removed by vacuum filtration and the filtrate was concentrated under reduced pressure. The residual syrup was taken up in a mixture of hexanes-ethyl acetate and charged on a silica gel column (25.56 g) that was eluted with hexanes-ethyl acetate (1:1). Combination of appropriate fractions, followed by concentration under reduced pressure gave 3, 4-bis-benzylthiobutanenitrile as a yellow-orange liquid (1.72 g).

(C) The product from part (B) (8.5 mmol) was diluted with equal volumes of acetic acid and acetic anhydride, then treated with 30% hydrogen peroxide (3 equivalents) in 1000 portions. After stirring overnight, the reaction mixture was diluted with water, and filtered. The damp solid was taken up in hot acetic acid from which it crystallized upon cooling. The white solid was collected by filtration, washed with acetic acid, and dried under vacuum to give the title compound in 27% yield (from benzyl mercaptan); mp: 160.8-161.8° C.

The 1H NMR spectrum for the compound was acquired in DMSO-d6 solution at 400 MHz by Spectral Data Services, Inc. Table 1 shows the chemical shift data (ppm) of NMR results.

TABLE 1

| Chemical Shift (ppm) | $RIV^a$ | Number of Protons | Multiplicity | Assignment |
|---|---|---|---|---|
| 1.04 | 6.29 | | d | IPA |
| 4.02 | 4.02 | | s | HOAc |
| 2.08 | 0.11 | | | impurity |
| 2.50 | | | | DMSO |
| 3.2-3.4 | ~20 | 2 | dq | $SO_2CH_2CHCH_2CN$ (2) |
| 3.4-3.6 | 10.00 | 1 | dd | $SO_2CH_2CHCH_2CN$ (1) |
| 3.33 | ~5 | | s | $H_2O$ |
| 3.8-3.9 | 1.23 | | m | IPA |
| 3.9-4.0 | 9.99 | 1 | dd | $SO_2CH_2CHCH_2CN$ |
| 4.1-4.3 | 10.07 | 1 | m | $SO_2CH_2CHCH_2CN$ |
| 4.34 | 1.25 | | d | impurity |
| 4.7-4.9 | 39.48 | 4 | m | $C_6H_5CH_2$ |
| 7.3-7.5 | 99.03 | 10 | d | $C_6H_5$ |
| 11.96 | 1.41 | | broad | HOAc |

The structure of 3, 4-bis-benzylsulfonylbutanenitrile comprises 19 protons. All protons are accounted for and occur at reasonable chemical shifts. Chemical shift assignments for the benzyl protons are unequivocal, as is that for the methine proton. The two split doublets at 3.4-3.6 ppm and 3.9-4.0 ppm are coupled to each other (J~14.5 Hz), and likely correspond to the α-sulfone-substituted methylene, which would be expected to occur at resonance(s) further downfield than the α-nitrile-substituted methylene. The complexity of the methylene multiplets may be indicative of hindered rotation in the molecule.

Example 2

Gel Formulation 1

Table 2 exemplifies one gel formulation containing 3, 4-bis-benzylsulfonylbutanenitrile.

TABLE 2

| | 5% Gel | 1% Gel |
|---|---|---|
| Active compound | 5.0% | 1.0% |
| Dow Corning Elastomer Blend EL-8050 ID | 61.4% | 63.4% |
| Labrafac Lipophile WL 1349 | 8.6% | 8.6% |
| Octisalate | 5.0% | 5.0% |
| Lauryl Lactate | 1.0% | 3.0% |
| Methyl Laurate | 5.0% | 7.0% |
| Dow Corning 556 Cosmetic Grade Fluid | 5.0% | 7.0% |
| Squalene | 2.0% | 2.0% |
| Sunflower Seed Oil | 2.0% | 2.0% |
| Diethylene Glycol Monoethyl Ether | 5.0% | 3.0% |
| Total | 100.0% | 100.0% |

Example 3

Anti-Inflammatory Activity of Active Compound by Topical Application in Mice 3, 4-Bis-benzylsulfonylbutanenitrile, prepared from Example 1, was used in this experiment. The test compound, indomethacin (positive control), and vehicle were evaluated for anti-inflammatory activity in a topical arachidonic acid-induced ear swelling model in mice.

Male ICR mice weighing 22±2 g were used and randomly divided; the test compound and vehicle control had 10 mice, and indomethacin had 5 mice. Arachidonic Acid (0.5 mg in 20 μl of acetone:ethanol/1:1) was applied topically to the anterior and posterior surfaces of the right ear of each mouse. Test substances and vehicle, as listed in Table 2 were similarly applied 30 min before and 15 min after arachidonic acid application. The thickness of the right ear and the left ear was measured and the difference calculated as an indication of the inflammation in the right ear. Ear swelling was measured by a Dyer model micrometer gauge at 60 and 90 minutes after arachidonic acid application as an index of inflammation. Percent inhibition was calculated according to the formula: Ic−It/Ic×100, where Ic and It refers to increase of ear thickness (mm) in control and treated mice, respectively. ANOVA and Dunnett's test were employed to ascertain significant difference between vehicle control and treated groups. Significance is set at P<0.05 level. The results measured at 90 minutes after arachidonic acid application are summarized in Table 3.

TABLE 3

| Test Substance | Conc mM | Dosage mg/20 μL | n | % Inhibition | P Value |
|---|---|---|---|---|---|
| Vehicle - acetone:ethanol (1:1) | NA | NA | 10 | NA | |
| Indomethacin (Positive control) | 14 | 0.1 | 5 | 58 | <0.001 |
| 3, 4-bis-benzylsulfonylbutanenitrile | 375 | 2.8 | 10 | 34 | 0.003 |

The tested compound resulted in 34% inhibition in the ear swelling induced by arachidonic acid, relative to that in the vehicle-treated group. The differences between treated mice and vehicle-treated mice were determined to be statistically significant (p-value by t-test was 0.003).

Example 4

Analgesic Activity of Active Compound by Oral Administration in Mice (Tail Flick Model)

The tail flick test is a test of the pain response in animals. The tail flick test is used in basic pain research and to measure the effectiveness of analgesics, by observing the tail flick reaction to heat in an animal. This test assesses the nociceptive response to a local pain stimulus, and the ability of a drug to inhibit this response.

Vehicle control (DMSO) and test compound 3, 4-bis-benzylsulfonylbutanenitrile in DMSO were administered by oral gavage to mice with a volume of 5 mL/kg, immediately prior to testing, at time zero. The test compound was administered at a dosage of 500 mg/kg in DMSO. Positive control morphine in water was administered at time zero by subcutaneous injection at 8 mg/kg to mice. The primary purpose of the positive control subcutaneous morphine group is for quality control, to confirm that the assay preforms consistently. The purpose of morphine is not to serve as a comparison with the test compound. Each group had 10 mice.

The response of mice to heat stimulus was evaluated by measuring the time of tail-flick or tail-flick latency from 49° C. water bath. Briefly, the animal was held with its tail hanging down. Approximately 2 inches of the tail was immersed in a beaker of water at 38±1° C. for about 30 seconds, and this was done twice to acclimate the animal to the procedure.

Subsequently, approximately 2 inches of the tail was immersed in a beaker of water at 49±1° C., at which point a timer was started. At the first sign of discomfort (whole body jerk, curvature or rapid movement of the tail), or at 30 second if the animal did not response, the timer was stopped, the latency time was recorded, and the tail was removed from the water.

Tail flick measurements were made at 0, 30, 60, and 120 minutes post administration of the dosage of test compound, vehicle, or morphine. An ANOVA was done, and if p<0.05, a Dunnett's t test was employed to calculate significant difference between vehicle control and test compound treated groups. A pairwise Student's t test was used to calculate differences between the morphine group and the control group. Results of tail flick response from each group are calculated as mean±SEM (standard error of mean). Analysis with p-values <0.05 is considered significant.

FIG. 1 shows the results of tail flick of mice treated with vehicle (DMSO, oral application), test compound (500 mg/kg in DMSO, oral application) and morphine (8 mg/kg in saline, subcutaneous application). The latency time of each group is calculated as mean±SEM and plotted against time, where * indicates p value <0.05 compared with vehicle-treated mice.

As shown in FIG. 1, morphine-treated mice (subcutaneous injection) show statistically significant tail flick latency at 30 and 60 minutes, but not 120 minutes post dosing, when compared with vehicle-treated mice. Mice treated with test compound by oral administration at 500 mg/kg show statistically significant tail flick latency at 120 minutes, when compared with vehicle-treated mice. The above results provide evidence that test compound when administered orally, is effective in treating nociceptive pain in an animal.

Example 5

Anti-inflammatory Activity of Active Compound in Mice by Oral Application (Prophetic Example)

The active compound 3, 4-bis-benzylsulfonylbutanenitrile is suspended in a vehicle (DMSO) to 5-15 mg/mL. The test compound, dexamethasone (positive control), and vehicle are orally administered to mice and evaluated for anti-inflammatory activity in the topical arachidonic acid induced ear swelling model in mice.

Male ICR derived mice are used in this experiment. 10 mice are used for each group (active compound, positive control, and vehicle). All animals are maintained in a controlled temperature (22-24° C.) and humidity (60%-70%) environment with 12-hour light/dark cycles for at least one week prior to use.

Arachidonic acid (0.5 mg in 20 μL acetone) is applied topically onto the anterior and posterior surfaces of the right ear of test animals to induce inflammation. Test compound in vehicle (10 mL/kg) and vehicle (10 mL/kg, 50-150 mg/kg) are orally administered by gavage 1 hour before arachidonic acid, whereas dexamethasone is orally administered by gavage 3 hour before arachidonic acid challenge. At 60 minutes and 90 minutes after arachidonic acid induction of ear edema, the thickness of the right ear and the left ear is measured and the difference calculated as an indication of the inflammation in the right ear. Significant activity is defined as a statistically significant inhibition (p-value determined by t-test was <0.05) in arachidonic acid induced ear swelling relative to the vehicle-treated group.

Example 6

Analgesic Activity of Active Compound by Oral Administration in Mice (Formalin Model, Prophetic Example)

Formalin test is a model of continuous pain resulting from formalin-induced tissue injury. Nociceptive and inflammatory pain is induced by injection of a dilute formalin solution into the paw, resulting in nocifensive behavior including paw flinching. The formalin model encompasses inflammatory, neurogenic, and central mechanism of pain. The early phase of pain (from 0 to about 10 minutes) is due to nociceptive mechanism and the late phase of pain (from 10-40 minutes) is due to a combination of inflammatory pain and nociceptive mechanism. Pain behavior is assessed using manual paw licking measurements. The endpoints of the study are the number of paw licking events. (Hunskaar et al., *Pain*, 30:103-114, 1987; Li et al., *Molecular Pain*, 6:11, 2010)

10 Mice per group are used in the study. Immediately prior to testing (at time 0), mice are restrained in a cloth and injected with 20 μL of a 5% formalin solution, subcutaneously into the dorsal surface of the left hind paw. Vehicle control (DMSO) and test compound 3, 4-bis-benzylsulfonylbutanenitrile (in DMSO) are administered by oral gavage with a volume of 5 mL/kg to mice. The amounts of test compound are 100 or 500 mg/kg per dose.

Positive control morphine in saline is administered by subcutaneous injection at 8 mg/kg to mice, immediately before formalin injection and testing at time zero.

Following formalin injection, animals are placed in individual cages, and manually observed for 60 minutes. The licking events are recorded in five minute intervals continuously for a total of 60 minutes.

The number of licking events at different time points post formalin injection of vehicle control, morphine-treated, and test compound-treated mice are plotted in 5 minute intervals.

The numbers of licking events per minute are calculated between 0-10 minutes and 10-40 minutes for vehicle, positive control, and test compound. A statistically significant reduction of licking event per minute is an indication that the test compound is effective in treating acute nociceptive pain (early phase) or inflammatory nociceptive pain (late phase).

Example 7

Analgesic Activity of Active Compound by Topical Administration in Mice (Formalin Model, Prophetic Example)

The animals and the treatment protocol are similar to those described in Example 6, except the following.

The test compound 3, 4-bis-benzylsulfonylbutanenitrile (375 mM in vehicle, n=10) and vehicle control (acetone:ethanol 1:1, n=10) are administered topically by submerging the mouse left hind paw in the respective solution for about 30 seconds. The paw is then withdrawn and wiped with tissue to avoid excess dermal drying.

Positive control morphine is administered by subcutaneous injection at 8 mg/kg in saline (n=10).

Morphine is subcutaneously administered once 15 minutes before formalin injection. The test compounds and vehicle control are topically administered twice (BID), at 60 minutes before formalin injection.

Following formalin injection, animals are placed in individual cages, and manually observed for 60 minutes. The licking events are recorded in five minute intervals continuously for a total of 40 minutes.

The number of licking events at different time points post formalin injection of vehicle control, morphine-treated, and test compound-treated mice are determined.

The numbers of licking events per minute are calculated between 0-10 minutes and 10-40 minutes for vehicle, positive control, and test compound. A two-sample t-test is done to compare the vehicle group with the test compound group. Significance is set at $P<0.05$ level.

Example 8

Analgesic Activity of Active Compound in Chronic Constriction Injury Model (Prophetic Example)

Peripheral nerve lesions may generate a syndrome comprising, in addition to spontaneous pain, exaggerated responses to light touch (tactile allodynia). Chronic constriction injury model is a neuropathic pain model.

Male Sprague Dawley rats are used. Under pentobarbital (50 mg/kg, 5 ml/kg, i.p.) anesthesia, the sciatic nerve is exposed at mid-thigh level. Four ligatures (4-0 chromic gut), about 1 mm apart, are loosely tied around the nerve. The animals are then housed individually in cages with soft bedding for 7 days before testing. Constriction of the sciatic nerve produces nerve injury and unilateral neuropathic pain.

On the day of experiments, the animals have no access to food overnight before testing. The rats are placed under inverted plexiglass cages on a wire mesh rack and allowed to acclimate for 20 to 30 minutes. Mechanic allodynia is evaluated by the Chaplan up/down method using von Frey filaments to the plantar surface of the left hind paw. See Chaplan, et al. *J. Neuroscience Methods*, 53: 55-63, 1994.

Rats are pre-selected for experimentation only if the pain threshold 7-14 days after nerve ligation (pre-treatment) is reduced by 10 grams of force relative to the response of the individual paw before nerve ligation (pre-ligation), namely, with clear presence of allodynia.

The active compound 3, 4-bis-benzylsulfonylbutanenitrile is prepared in the gel formulation according to Example 2.

Active compound in gel formulation (1-5%, topical administration), active compound in DMSO (500 mg/kg, oral administration), morphine (positive control, subcutaneous, 8 mg/kg in saline), topical vehicle (gel formulation without the active compound), and oral vehicle (DMSO) are evaluated.

Test substance or vehicle is either administered orally or topically to the plantar surface of the left hind paw. The mechanical allodynia test is performed 30 min before (pre-treatment) and 1 and 3 hours after a single dose of test substance or vehicle (post treatment). Paw withdraw thresholds of control and tested compound are measured.

Example 9

Treatment of Knee Pain by Topical Administration (Prophetic Example)

Objectives:

To investigate the efficacy of the active compound in a topical gel formulation in human patients with mild to severe knee pain associated with osteoarthritis following temporary cessation of standard NSAID therapy. The focus of this study is on the symptoms caused by painful arthritis.

The clinical trial is utilizing osteoarthritis of the knee as a well-established paradigm for other musculoskeletal disorders.

Topical Formulation:

The gel formulations containing the active compound 3, 4-bis-benzylsulfonylbutanenitrile at 1% and 5% (Example 2) are used in this example. Placebo contains the same gel without the active compound.

Methodology:

A randomized, double-blind, placebo controlled, parallel treatment multicenter clinical activity study.

Patients with painful osteoarthritis of the knee, controlled by a stable dose of standard NSAID therapy for at least 2 months, discontinue use of the NSAIDs for a 7-day washout period. Patients are then randomized in a 1:1:1 ratio (1% active gel, 5% active gel, placebo). A total of up to 150 patients are enrolled.

The active gel or placebo is applied to the affected knee 3 times a day for 12 weeks for a total of 252 treatments given every 4-6 hours while awake.

Patients are treated for 12 weeks and followed up for a further 4 weeks. NSAIDs may be restarted after the Week 12 visit.

Criteria for Evaluation:

Safety:

Adverse Events (AEs) throughout the study.

Physical examination at enrollment (−7 days, start of NSAID washout period), Baseline (Day 1, start of treatment), Week 12 and Week 16.

Vital signs at enrollment (−7 days, start of NSAID washout period), Baseline (Day 1, start of treatment) and Weeks 2, 4, 6, 12 and 16.

Clinical laboratory measurements at Baseline (Day 1), Week 4, 8, 12 and 16.

Clinical Activity:

The primary clinical activity parameters are the measurement of pain in the target joint, as quantified by the Visual Analog Scale (VAS) and the Western Ontario and McMaster University (WOMAC) Index pain subscale. The effect of treatment on swelling, tenderness and inflammation of the knee is recorded, also the time to reduction or eradication of pain after treatment is recorded.

Study Endpoints:

The primary clinical activity endpoint is:

Change from Baseline (Day 1) to Week 12 in WOMAC functional disability index pain subscale (Scale 0-20)

The secondary clinical activity endpoints are:

Change from Baseline (Day 1) to Week 12 in WOMAC functional disability index subscales:

Stiffness (Scale 0-8).

Physical function (Scale 0-68).

Change from Baseline (Day 1) to Week 12 in VAS pain score (0-100).

Change from Baseline (Day 1) to Week 2 in VAS pain score (0-100).

Change in investigator evaluation of swelling, tenderness and inflammation between Baseline (Day 1) and Weeks 4 and 12 after the first application on Day 1.

Time to reduction or eradication of pain subsequent to each topical application of active gel or placebo gel.

Use of rescue medication (APAP).

Example 10

Treatment of Knee Pain by Oral Administration (Prophetic Example)

The design and protocols of this experiment are similar to those described in Example 9, except the active compounds and placebo are applied by an oral route.

Oral Formulation:

Tablet formulations containing 10, 100, or 1000 mg of the active compound 3, 4-bis-benzylsulfonylbutanenitrile are used in this example. Placebo has the same tablet formulation without the active compound.

Methodology:

Patients are then randomized in a 1:1:1:1 ratio (10 mg:100 mg:1000 mg: placebo). A total of up to 200 patients are enrolled.

The active tablet or placebo is administered orally to each patient two times a day for 12 weeks for a total of 168 treatments given every 12 hours while awake. Patients are treated for 12 weeks and followed up for a further 4 weeks.

Criteria for evaluation are the same as those described in Example 9.

Example 11

Treatment of Arthritis (Prophetic Example)

Zymosan injected directly into the knee joint of mice elicits an inflammatory response and is used as a model of arthritis (Verschure et al, Ann. Rheum Dis. 53:455-460, 1994). Endpoints measured in this model include knee joint swelling score, cytokine levels in the synovial tissue and microscopic pathology of the knee.

Active compound 3, 4-bis-benzylsulfonylbutanenitrile (in vehicle) and vehicle control (1% Tween 80 in water suspension or other lipid-based pharmaceutically acceptable carrier) are administered by oral gavage to mice with a volume of 5 mL/kg. The oral dosage of active compound is 500 mg/kg mouse.

There are 5 mice per group, with a total of 10 knees injected. On Day 1, C57BL6 mice are dosed (500 mg/kg) with active compound or vehicle twice on Hours 0 and 12. On Day 2, mice are dosed with active compound or vehicle on Hour 24, then injected intra-articularly with 180 µg of zymosan (6 µL) into both knee joints on Hour 25, and then dosed a second time on Hour 36 with each active compound or vehicle. On Day 3, mice are again dosed with active compound or vehicle on Hour 48. Two hour post-dosing on Hour 50, knees are scored for edema, synovial tissue is collected for measurement of cytokine levels, and knee joints are processed for histopathology for analysis of inflammatory immune cell influx into the joint. Macroscopic joint swelling is assessed on all knees after the skin is removed using a scoring system ranging from 0 to 3, with 0 being no swelling and 3 being severe swelling. Synovial tissue is taken from 5 knees for measurement of mouse interleukin-10, interleukin-6, and interleukin-1 receptor antagonist levels. The remaining 5 knees are processed for microscopic pathology for assessment of cellular influx into the site of inflammation.

Results for each group are presented as mean±standard error of mean and statistical evaluation is performed.

Treatment with active compound is expected to result in decreased inflammation as measured by a decrease in joint swelling, decrease in cytokine levels and decrease influx of inflammatory cells to the site of inflammation.

Example 12

Treatment of Gout (Prophetic Example)

Monosodium urate monohydrate (MSU) crystals injected in combination with a free fatty acid (FFA) directly into the knee joint of mice elicits an inflammatory response and is used as a model of gout (Joosten et al, Arthritis & Rheumatism, 62:3237-3248, 2010). Endpoints measured in this model include knee joint swelling score, cytokine levels in the synovial tissue and microscopic pathology of the knee.

Active compound 3, 4-bis-benzylsulfonylbutanenitrile (in vehicle) and vehicle control (1% Tween 80 in water suspension or other lipid-based pharmaceutically acceptable carrier) are administered by oral gavage to mice with a volume of 5 mL/kg. The oral dosage of active compound is 500 mg/kg mouse.

There are 5 mice per group, with a total of 10 knees injected. On Day 1, C57BL6 mice are dosed (500 mg/kg/dose) with active compounds or vehicle twice on Hours 0 and 12. On Day 2, mice are dosed with active compounds or vehicle on Hour 24, then injected intra-articularly with MSU crystals (300 µg) and C18:0 FFA (200 µM, 10 µL) on Hour 25. Three hours later (Hour 28), knees are scored for edema, synovial tissue is collected for measurement of cytokine levels, and knee joints are processed for histopathology for analysis of inflammatory immune cell influx into the joint. Macroscopic joint swelling is assessed on all knees after the skin is removed using a scoring system ranging from 0 to 3, with 0 being no swelling and 3 being severe swelling. Synovial tissue is taken from 5 knees for measurement of mouse interleukin-1β, interleukin-6, and interleukin-1 receptor antagonist levels. The remaining 5 knees are processed for microscopic pathology for assessment of cellular influx into the site of inflammation.

Results for each group are presented as mean±standard error of mean and statistical evaluation is performed.

Treatment with active compound is expected to result in decreased inflammation as measured by a decrease in joint swelling, decrease in cytokine levels and decrease influx of inflammatory cells to the site of inflammation.

Example 13

Treatment of Contact Dermatitis (Prophetic Example)

Mice dermally sensitized and challenged by dinitrofluorobenzene (DNFB) are used as a model of contact dermatitis (Saint-Mezard, J Invest Dermatol, 120:641-647, 2003).
Sensitization and Challenging:

There are 5 mice per group. Each mouse is sensitized with 0.5% DNFB (vehicle=4:1 (vol/vol) acetone:olive oil) topically on the shaved abdomen, 6 days before challenge. The right ears of the mice are then challenged with a topical application of 0.2% DNFB in vehicle. The left ears of the mice receive the vehicle as control.
Oral Administration:

Active compound 3, 4-bis-benzylsulfonylbutanenitrile (in vehicle) and vehicle control (1% Tween 80 in water suspension or other lipid-based pharmaceutically acceptable carrier) are administered by oral gavage to mice with a volume of 5 mL/kg. The oral dosage of active compound is 500 mg/kg mouse.

Before challenge, each group of mice receive oral dosages of active compound or vehicle at 24 hours, 12 hours, and 2 hours before the challenge.

After challenge, the same oral dosages of active compound or vehicle are given to each mouse 7 hours, 22 hours, 31 hours, 46 hours, and 55 hours after the challenge. The thickness of the left and right ears are measured before challenge, and 24, 48, and 72 hours after challenge. Results are expressed as net swelling: thickness after challenge minus thickness before challenge. Net swelling of treated mice vs. control mice are compared.
Topical Administration:

Active compound 3, 4-bis-benzylsulfonylbutanenitrile prepared in vehicle (1:1; acetone:ethanol) at 375 mM and vehicle alone are topically applied to both ears of the mice in a volume of 20 µl.

The topical doses are given after challenge to each mouse 7 hours, 22 hours, 31 hours, 46 hours, and 55 hours after the challenge. The thickness of the left and right ears are measured before challenge, and 24, 48, and 72 hours after challenge. Results are expressed as net swelling: thickness after challenge minus thickness before challenge. Net swelling of treated mice vs. control mice are compared.

Example 14

Treatment of Atopic Dermatitis (Prophetic Example)

Objectives:

To investigate the efficacy of 3, 4-bis-benzylsulfonylbutanenitrile in patients having atopic dermatitis.
Topical Formulation:

3, 4-bis-benzylsulfonylbutanenitrile is prepared as a gel formulation according to Example 2. Placebo contains the same gel ingredients without the active compound.
Oral Formulation:

Capsules or tablets each containing 100-800 mg of the active compound 3, 4-bis-benzylsulfonylbutanenitrile are used in this example. Placebo capsules or tablets do not contain the active compound.
Methodology:

This is a randomized, double-blind, placebo controlled, parallel treatment clinical activity study.

Male and female patients with mild to severe atopic dermatitis are enrolled after discontinuation of all treatments for atopic dermatitis for a period of 4 weeks before study initiation. Patients are randomized in a 1:1 ratio (active gel, placebo). A total of 300 patients are enrolled and treated.

The active gel or placebo is applied twice a day to affected areas of the body for 12 weeks.

The capsules or tablets are orally administered to patients 1-4 times a day for 12 weeks.

The treatment results are evaluated at 2 week intervals until week 12 and then at 4 weeks after discontinuation of the study medication.
Criteria for Evaluation:
Safety:

Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).
Efficacy:

Efficacy is Evaluated Utilizing:

1. an overall assessment of disease severity at study entry and at 2 week intervals until week 12 and subsequently at 4 weeks after study medication discontinuation. The investigator global assessment, IGA, is based upon a rating scale of 0 to 4 with 0=none or clear, 1=almost clear, 2=mild disease involvement, 3=moderate disease involvement, and 4=severe disease involvement, and:

2. separate evaluation of a representative target atopic dermatitis area of involvement for erythema, induration, lichenification, scaling, and oozing and crusting with each parameter rated on a 0-4 scale with 0=none or clear, 1=almost clear, 2=mild disease involvement, 3=moderate disease involvement, and 4=severe disease involvement.

Statistical analyses of each of these efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

Example 15

Treatment of Psoriasis (Prophetic Example)

Objectives:
To investigate the efficacy of the 3, 4-bis-benzylsulfonylbutanenitrile in patients having psoriasis vulgaris.
Topical Formulation:
3, 4-bis-benzylsulfonylbutanenitrile is prepared as a gel formulation according to Example 2. Placebo contains the same gel ingredients without the active compound.
Oral Formulation:
Capsules or tablets each containing 100-800 mg of the active compound 3, 4-bis-benzylsulfonylbutanenitrile are used in this example. Placebo capsules or tablets do not contain the active compound.
Methodology:
This is a randomized, double-blind, placebo controlled, parallel treatment clinical activity study.
Male and female patients with mild to severe psoriasis vulgaris are enrolled. Patients discontinue all treatments for psoriasis for a period of 4 weeks before study initiation. Patients are randomized in a 1:1 ratio (active gel, placebo). A total of 200 patients are enrolled and treated.
The active gel or placebo is applied twice a day to affected areas of the body for 12 weeks.
The capsules or tablets are orally administered to patients 1-4 times a day for 12 weeks.
The treatment results are evaluated at 2 week intervals until week 12 and then at 4 weeks after discontinuation of the study medication.
Criteria for Evaluation:
Safety:
Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).
Efficacy:
Efficacy is Evaluated Utilizing:
1. an overall assessment of disease severity at study entry and at 2 week intervals until week 12 and subsequently at 4 weeks after study medication discontinuation. The investigator global assessment, IGA, is based upon a rating scale of 0 to 4 with 0=none or clear, 1=almost clear, 2=mild disease involvement, 3=moderate disease involvement, and 4=severe disease involvement, and:
2. separate evaluation of a representative target psoriasis lesion for erythema, scaling, and thickness of each parameter rated on a 0-4 scale with 0=none or clear, 1=almost clear, 2=mild disease involvement, 3=moderate disease involvement, and 4=severe disease involvement.

Statistical analyses of each of the efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

Example 16

Treatment of Acne (Prophetic Example)

Objectives:
To investigate the efficacy of the 3, 4-bis-benzylsulfonylbutanenitrile in patients having acne vulgaris.
Topical Formulation:
3, 4-bis-benzylsulfonylbutanenitrile is prepared as a gel formulation according to Example 2. Placebo contains the same gel ingredients without the active compound.
Oral Formulation:
Capsules or tablets each containing 100-800 mg of the active compound 3, 4-benzylsulfonylbutanenitrile are used in this example. Placebo capsules or tablets do not contain the active compound.
Methodology:
This is a randomized, double-blind, placebo controlled, parallel treatment clinical activity study.
Male and female patients with mild to severe acne vulgaris are enrolled. Patients discontinue all treatments for acne for a period of 4 weeks before initiation of the study. Patients are randomized in a 1:1 ratio (active gel, placebo). A total of 500 patients are enrolled and treated.
The active gel or placebo is applied twice a day to affected areas of the body for 12 weeks.
The capsules or tablets are orally administered to patients 1-4 times a day for 12 weeks.
The treatment results are evaluated at 2 week intervals until week 12 and then at 4 weeks after discontinuation of the study medication.
Criteria for Evaluation:
Safety:
Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).
Efficacy:
Efficacy is Evaluated Utilizing:
1. an overall assessment of disease severity at study entry and at 2 week intervals until week 12 and subsequently at 4 weeks after discontinuation of the study medication.
The investigator global assessment, IGA, is based upon a rating scale of 0 to 4 with 0=none or clear, 1=almost clear, 2=mild disease involvement, 3=moderate disease involvement, and 4=severe disease involvement, and:
2. separate counts of all types of acne lesions i.e. open and closed comedones, papules, pustules, nodules, and cysts.

Statistical analyses of each of the efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

It is to be understood that the foregoing describes preferred embodiments of the present invention and that modifications may be made therein without departing from the scope of the present invention as set forth in the claims.

What is claimed is:

1. A compound of 3, 4-bis-benzylsulfonylbutyronitrile or a pharmaceutically acceptable salt thereof.

2. A pharmaceutical composition comprising a pharmaceutically acceptable carrier and the compound of claim 1, or a pharmaceutically acceptable salt thereof.

3. The pharmaceutical composition according to claim 1, wherein the compound has at least 90% (w/w) purity, and the composition is in a topical form of gels, creams, lotions, ointments, solutions, suspensions, sprays, or patches.

4. The pharmaceutical composition according to claim 3, wherein the pharmaceutically acceptable carrier is an emollient selected from the group consisting of: lauryl lactate, diethylene glycol monoethyl ether, caprylic/capric triglyceride, octisalate, silicone fluid, squalene, and sunflower oil.

5. The pharmaceutical composition according to claim 2, wherein the pharmaceutically acceptable carrier is a permeation enhancer selected from the group consisting of lactate esters and diethylene glycol monoethyl ether.

6. The pharmaceutical composition according to claim 5, further comprising acrylates/C10-30 alkyl and tris(2-hydroxyethyl)amine.

7. The pharmaceutical composition according to claim 2, wherein the compound has at least 90% (w/w) purity, and the composition is in an oral form of tablets, capsules, granules, powders, or syrups.

8. A process for preparing the compound of claim 1, comprising the steps of:
    (a) reacting benzyl mercaptan with 4-bromo-2-butenenitrile in a basic condition to produce 3,4-bis-benzylthiobutyronitrile, and
    (b) oxidizing 3,4-bis-benzylthiobutyronitrile with peroxide to produce 3,4-bis-benzylsulfonylbutyronitrile.

9. The process according to claim 8, further comprising a step of reacting bromine $Br_2$ with allyl cyanide in a basic condition to prepare 4-bromo-2-butenenitrile.

* * * * *